US012239678B2

(12) United States Patent
Archer et al.

(10) Patent No.: US 12,239,678 B2
(45) Date of Patent: Mar. 4, 2025

(54) YEAST FOR THE TREATMENT OF ALLERGY

(71) Applicant: MILMED UNICO AB, Stockholm (SE)

(72) Inventors: Trevor Archer, Floda (SE); Tomas Lenz, Örebro (SE)

(73) Assignee: MILMED UNICO AB, Stockholm (SE)

( * ) Notice: Subject to any disclaimer, the term of this patent is extended or adjusted under 35 U.S.C. 154(b) by 0 days.

(21) Appl. No.: 17/766,959

(22) PCT Filed: Oct. 7, 2020

(86) PCT No.: PCT/SE2020/050958

§ 371 (c)(1),
(2) Date: Apr. 6, 2022

(87) PCT Pub. No.: WO2021/071413

PCT Pub. Date: Apr. 15, 2021

(65) Prior Publication Data

US 2024/0066083 A1 Feb. 29, 2024

(30) Foreign Application Priority Data

Oct. 7, 2019 (SE) .................................... 1951142-7

(51) Int. Cl.

| | |
|---|---|
| ***A61K 36/064*** | (2006.01) |
| ***A61P 37/08*** | (2006.01) |
| ***C12N 1/20*** | (2006.01) |
| ***C12N 13/00*** | (2006.01) |
| ***C12R 1/86*** | (2006.01) |
| ***C12R 1/865*** | (2006.01) |

(52) U.S. Cl.

CPC ............ *A61K 36/064* (2013.01); *A61P 37/08* (2018.01); *C12N 1/20* (2013.01); *C12N 13/00* (2013.01); *C12R 2001/86* (2021.05); *C12R 2001/865* (2021.05)

(58) Field of Classification Search

CPC .. A61K 36/064; A61K 36/06; A61K 41/0023; A61K 41/00; A61P 37/08; A61P 11/00; A61P 11/06; A61P 27/14; C12N 1/20; C12N 13/00; C12N 1/18; C12R 2001/86; C12R 2001/865; A61N 5/00; A61N 5/02

See application file for complete search history.

(56) References Cited

U.S. PATENT DOCUMENTS

| | | |
|---|---|---|
| 2004/0001860 A1 | 1/2004 | Cheung |
| 2004/0005680 A1 | 1/2004 | Cheung |

FOREIGN PATENT DOCUMENTS

| | | | |
|---|---|---|---|
| JP | 200568092 | A | 3/2005 |
| JP | 2005104943 | A | 4/2005 |
| JP | 2008182900 | A | 8/2008 |
| JP | 2010209015 | A | 9/2010 |
| JP | 4712289 | B2 | 6/2011 |
| JP | 2013503138 | A | 1/2013 |
| JP | 2013247939 | A | 12/2013 |
| JP | 6002452 | B2 | 10/2016 |
| KR | 101898508 | B1 | 9/2018 |
| WO | 2004108919 | A1 | 12/2004 |
| WO | 2011023769 | A1 | 3/2011 |

OTHER PUBLICATIONS

Moyad MA, Robinson LE, Kittelsrud JM, Reeves SG, Weaver SE, Guzman AI, Bubak ME. Adv Ther. Aug. 2009;26(8):795-804. doi: 10.1007/s12325-009-0057-y. Epub Aug. 12, 2009. Erratum in: Adv Ther. Aug. 2019;36(8):2191. PMID: 19672568. (Year: 2009).*

Moyad MA, Robinson LE, Zawada ET, Kittelsrud J, Chen DG, Reeves SG, Weaver S. Immunogenic yeast-based fermentate for cold/flu-like symptoms in nonvaccinated individuals. J Altern Complement Med. Feb. 2010;16(2):213-8. doi: 10.1089/acm.2009.0310. PMID: 20180695; PMCID: PMC6498863. (Year: 2010).*

Bower et al., Neurology, 2006, vol. 67, p. 494-496. (Year: 2006).*

Luciano Furia et al: "Effect of Millimeter-Wave Irradiation on Growth of *Saccharomyces cerevisiae*", IEEE Transactions on Biomedical Engineering, IEEE, USA, vol. BME-19, No. 11 , Nov. 1, 1986 (Nov. 1, 1986), pp. 993-999, XP011173859, ISSN: 0018-9294.

Andrei G Pakhomov A et al: "Low-Intensity Millimeter Waves as a Novel Therapeutic Modality", IEEE Transactions on Plasma Science, IEEE Service Center, Piscataway, NJ, US, vol. 28, No. 1, Jan. 1, 2000 (Jan. 1, 2000), XP011045464, ISSN: 0093-3813, DOI: 10.1109/27.842821.

Trevor Archer et al: "Milmed Treatment Alleviates Symptoms of Allergy and Improves General Health", Journal of Immunology and Allergy, vol. 1, No. 3, Jun. 11, 2020 (Jun. 11, 2020) , pp. 3-11, XP093101064, DOI: 10.37191/Mapsci-2582-6549-1(3)-017 * the whole document.

Trevor Archer et al: "Amelioration For Allergic Rhinitis and Asthma: The Treated Yeast Milmed and Physical Exercise", Journal of Immunology and Allergy, vol. 1, No. 1, Nov. 19, 2019 (Nov. 19, 2019), pp. 1-6, XP093101165, ISSN: 2582-6549, DOI: 10.37191/Mapsci-2582-6549-1(1)-003 * the whole document *.

Erixon RM, et al., Amelioration For Allergic Rhinitis and Asthma: The Treated Yeast Milmed and Physical Exercise, J Immuno Allerg. Published Nov. 19, 2019.

Fonseca VMB, Milani TMS, Prado R, Bonato VLD, Ramos SG, Martins FS, Vianna EO, Borges MC. Oral administration of *Saccharomyces cerevisiae* UFMG A-905 prevents allergic asthma in mice. Respirology. Jul. 2017;22(5):905-912. doi: 10.1111/resp.12990. Epub Feb. 6, 2017. PMID: 28166610.

(Continued)

*Primary Examiner* — Kade Ariani

(74) *Attorney, Agent, or Firm* — Renner, Otto, Boisselle & Sklar, LLP

(57) ABSTRACT

A yeast cell for use in the treatment and/or alleviation of allergy and/or symptoms caused by allergy, wherein the yeast cell has been treated with electromagnetic waves in the range of 1 GHz to 300 GHz, or said yeast cell has been grown from a yeast cell treated with electromagnetic waves in the range of 1 GHz to 300 GHz, and composition comprising such a yeast cell.

19 Claims, 1 Drawing Sheet

(56) References Cited

OTHER PUBLICATIONS

Yeh CY, Jung CJ, Huang CN, Huang YC, Lien HT, Wang WB, Wang LF, Chia JS. A legume product fermented by *Saccharomyces cerevisiae* modulates cutaneous atopic dermatitis-like inflammation in mice. BMC Complement Altern Med. Jun. 18, 2014;14:194. doi: 10.1186/1472-6882-14-194. PMID: 24939647; PMCID: PMC4074418.

Archer T, Fredriksson A. The yeast product Milmed enhances the effect of physical exercise on motor performance and dopamine neurochemistry recovery in MPTP-lesioned mice. Neurotox Res. Oct. 2013;24(3):393-406. doi: 10.1007/s12640-013-9405-4. Epub Jul. 27, 2013. PMID: 23893731.

Archer T. et al., 'Mil med Treatment Alleviated or Abolished Allergy', J Immuno Allerg. Mar. 2, 2020, vol. 1, pp. 1-13; whole document.

International Search Report corresponding to Application No. PCT/SE2020/050958 mailed Oct. 21, 2020.

* cited by examiner

YEAST FOR THE TREATMENT OF ALLERGY

This application is a national phase of International Application No. PCT/SE2020/050958 filed Oct. 7, 2020, which claims priority to Swedish Application No. 1951142-7 filed Oct. 7, 2019, the entire disclosures of which are hereby incorporated by reference.

TECHNICAL FIELD

The present disclosure relates to a yeast cell for use in the treatment and/or alleviation of allergy and/or symptoms caused by allergy, as well as a composition comprising said yeast cell.

BACKGROUND

In the developed world, about 20% of the population is affected by allergic rhinitis, about 6% of the population has at least one food allergy, and about 20% have atopic dermatitis at some point in time. In some countries, up to 18% of the population has asthma. Rates of many allergic diseases appear to be increasing. More than 150 million Europeans suffer from chronic allergic diseases and the current prediction is that by 2025 half of the entire EU population will be affected (EAACI, 2016).

An allergy is a chronic condition involving an abnormal reaction to an ordinarily harmless substance called an allergen. Allergens can include aeroallergens such as dust mite, mold, and tree weed and grass pollen, as well as food allergens such as milk, egg, soy, wheat, nut or fish proteins. Symptoms of allergy may include red eyes, an itchy rash, itching in the nose, roof of the mouth, throat, eyes, sneezing, a stuffy nose (congestion), a runny nose, tearing eyes, shortness of breath, or swelling. Food allergies may present with vomiting, diarrhea, respiratory symptoms or anaphylaxis immediately after ingestion of the allergen.

These diseases include hay fever (allergic rhinitis), asthma, allergic eyes (allergic conjunctivitis), allergic eczema, hives (urticaria), and allergic shock (also called anaphylaxis and anaphylactic shock).

Hay fever (allergic rhinitis) is the most common of the allergic diseases and refers to seasonal nasal symptoms that are due to pollens. Year round or perennial allergic rhinitis is usually due to indoor allergens, such as dust mites or molds. The most common symptoms include runny nose, stuffy nose, sneezing, nasal itching (rubbing), itchy ears and throat and post nasal drip (throat clearing).

Asthma (such as symptomatic asthma) is a breathing problem that results from the inflammation and spasm of the lung's air passages (bronchial tubes). Asthma is most often, but not always, related to allergies. Common symptoms include shortness of breath, wheezing, coughing and chest tightness. The expression "symptomatic asthma" is applied according to patients' description of their allergy problems.

Allergic eyes (allergic conjunctivitis) is inflammation of the tissue layers (membranes) that cover the surface of the eyeball and the undersurface of the eyelid. The inflammation occurs as a result of an allergic reaction. Common symptoms are redness under the lids and of the eye overall, watery, itchy eyes and swelling of the membranes.

Allergic eczema is an allergic rash that is usually not caused by skin contact with an allergen and features the following symptoms itching, redness, and or dryness of the skin, rash on the face, especially children, and rash around the eyes, in the elbow creases, and behind the knees, especially in adults.

Hives (urticaria) are skin reactions that appear as itchy swellings and can occur on any part of the body. Hives can be caused by an allergic reaction, such as to a food or medication, but they also may occur in non-allergic people. Typical hive symptoms are raised red welts and intense itching.

Treatments for allergies include avoiding known allergens and the use of medications such as antihistamines and steroids. These may be in the form of pills or liquid, nasal sprays, or eyedrops. Although newer generation of antihistamines has improved, people may still experience side-effects, such as headache, tiredness, dizziness, dry mouth, vision changes and excitability/nervousness. Side-effects of corticosteroid nasal sprays include nosebleeds, stinging in the nose and dryness of the nose, nausea and dizziness.

In addition, several complementary health approaches have been studied for allergic rhinitis and there is some evidence that a few may be helpful. Probiotics (live microorganisms that may have health benefits) have been investigated for diseases of the immune system, including allergies. For example, JP 6 002 452 discloses a *Saccharomyces cerevisiae* yeast as useful for prevention and treatment of various immunological diseases by suppressing production of IgE causing type I allergy symptoms and JP 4 712 289 discloses a mixture of *Saccharomyces* and lactic acid bacteria for the prevention of food allergy. Although some studies have had promising results, the overall evidence on probiotics and allergic rhinitis is inconsistent.

Thus, there is a need for new compositions and methods allowing for improved treatment or alleviation of allergy and/or symptoms associated with allergy.

An object of the present invention is to overcome these problems.

SUMMARY

According to a first aspect, the above and other objects of the invention are achieved, in full or at least in part, by a yeast cell as defined by claim 1. According to this claim the above object is achieved by a yeast cell for use in the treatment and/or alleviation of allergy and/or symptoms caused by allergy, wherein the yeast cell has been treated with electromagnetic waves in the range of 1 GHz to 300 GHz, or said yeast cell has been grown from a yeast cell treated with electromagnetic waves in the range of 1 GHz to 300 GHz. The yeast cells may be grown from a yeast cell treated with electromagnetic waves in the range of 1 GHz to 300 GHz for several generations, such as up to 300, 200 or 100 generations, such as up to 90, 80, 70, 60 or 50 generations, such as 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3 or 2 generations.

An advantage with the yeast cell according to the present disclosure is that it allows for improved and cost-effective treatment and/or alleviation of allergy and/or symptoms caused by allergy.

In a second aspect, a composition comprising at least on yeast cell according to the present disclosure and an excipient and/or carrier is provided. The composition may be for use in the treatment and/or alleviation of allergy and/or symptoms caused by allergy.

Further advantageous features of the invention and its embodiments are defined in the appended claims and in the detailed description.

Other objectives, features and advantages of the present invention will appear from the following detailed disclosure, from the attached claims, as well as from the drawings. It is noted that the invention relates to all possible combinations of features.

Generally, all terms used in the claims are to be interpreted according to their ordinary meaning in the technical field, unless explicitly defined otherwise herein. All references to "a/an/the [element, device, component, means, step, etc.]" are to be interpreted openly as referring to at least one instance of said element, device, component, means, step, etc., unless explicitly stated otherwise. The steps of any method disclosed herein do not have to be performed in the exact order disclosed, unless explicitly stated.

As used herein, the term "comprising" and variations of this term are not intended to exclude other additives, components, integers or steps.

BRIEF DESCRIPTION OF THE DRAWINGS

Further objects, features and advantages will appear from the following detailed description, with reference being made to the accompanying drawings, in which.

DETAILED DESCRIPTION

Figure 1A:
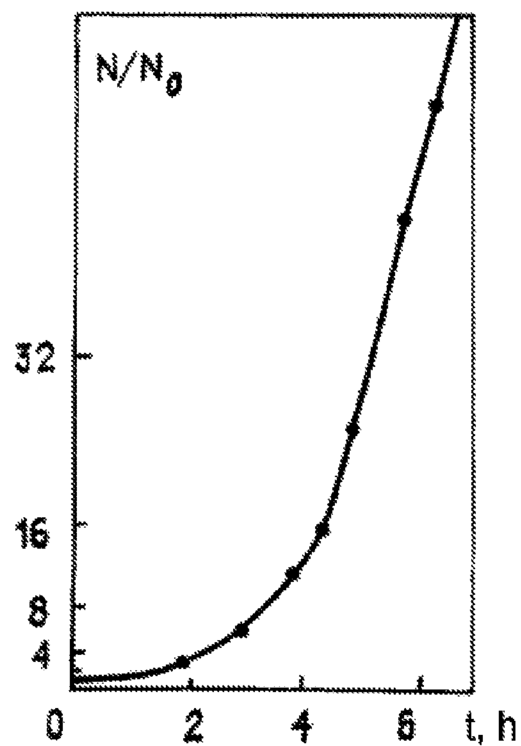
FIG. 1A is a diagram showing a growth curve of untreated yeast cells.

The use of low-intensity electromagnetic millimeter waves within non-traditional areas, such as medicine, biology and biotechnology is a trend that originated in Russia in the middle of the 1960s.

It has now surprisingly been found that a yeast cell treated with electromagnetic waves in the range of 1 GHz to 300 GHz (a so called treated yeast cell or treated yeast) or a yeast cell grown from a treated yeast cell are effective in the treatment and/or alleviation of allergy and/or symptoms caused by allergy. An advantage with the yeast cell according to the present disclosure is that it allows for improved and cost-effective treatment and/or alleviation of allergy and/or symptoms caused by allergy.

The electromagnetic waves may be delivered with any electronic or photonic device known within the art. The electromagnetic waves may have a power density below 1 mW/cm$^2$, such as about 0.1 mW/cm$^2$, such as between 0.004 mW/cm$^2$ and 0.2 mW/cm$^2$.

According to one embodiment, the allergy is selected from the group consisting of allergic rhinitis, mite allergy, fur allergy, seasonal allergy (also known as hay fever), food allergy; and/or wherein the symptoms caused by allergy is chosen from the group consisting of atopic dermatitis (eczema), asthma, and/or rhinitis.

The allergy may be caused by an allergen selected from the group consisting of mite, pollen, grass, dust, animal hair, animal dander, or animal urine. The animal hair may be from a domestic mammal, such as a horse, cow, rabbit, cat or dog, especially from horse, cat or dog. The animal dander may be from a domestic mammal, such as a horse, cow, rabbit, cat or dog, especially from horse, cat or dog. The animal urine may be from a domestic mammal, such as a horse, cow, rabbit, cat or dog, especially from horse, cat or dog.

According to another embodiment, the allergy is caused by an allergen selected from the group consisting of mite, pollen, animal hair, and animal dander.

According to yet another embodiment, said electromagnetic waves are in the range from about 1 GHz to about 200 GHz, such as 10 to 100 GHz, such as 30 to 70 GHz, such as 40 to 65 GHz. The oscillation frequency may be within the range from about 35 to about 65 GHz. The oscillation frequency may be 42.2 GHz.

The electromagnetic waves may be delivered with any electronic or photonic device known within the art. The electromagnetic waves may have a power density below 1 mW/cm$^2$, such as between 0.004 mW/cm$^2$ and 0.2 mW/cm$^2$, such as about 0.1 mW/cm$^2$.

According to a further embodiment, said electromagnetic waves are chosen from group consisting of: 40 GHz, 41 GHz, 42 GHz, 43 GHz, 44 GHz, 45 GHz, 46 GHz, 47 GHz, 48 GHz, 49 GHz, 50 GHz, 51 GHz, 52 GHz, 53 GHz, 54 GHz, 55 GHz, 56 GHz, 57 GHz, 58 GHz, 59 GHz, 60 GHz, 61 GHz, 62 GHz, 63 GHz, 64 GHz, and 65 GHz. The skilled person realizes that the frequencies above are lifted/depressed to the closest complete number without decimal points. Thus, e.g. 40 GHz shall be understood as 40±0.5. The electromagnetic waves may be delivered with any electronic or photonic device known within the art. The electromagnetic waves may have a power density below 1 mW/cm$^2$, such as between 0.004 mW/cm$^2$ and 0.2 mW/cm$^2$, such as about 0.1 mW/cm$^2$.

In one specific embodiment, the oscillation frequency is 42194±10 MHz and linearly modulated within a 100 MHz band around this frequency. The electromagnetic waves may be delivered with any electronic or photonic device known within the art. The electromagnetic waves may have a power density below 1 mW/cm$^2$, such as between 0.004 mW/cm$^2$ and 0.2 mW/cm$^2$, such as about 0.1 mW/cm$^2$.

In another specific embodiment, the oscillation frequency is 53534±10 MHz and linearly modulated within a 50 MHz band around this frequency. The electromagnetic waves may be delivered with any electronic or photonic device known within the art. The electromagnetic waves may have a power density below 1 mW/cm$^2$, such as between 0.004 mW/cm$^2$ and 0.2 mW/cm$^2$, such as about 0.1 mW/cm$^2$.

In another specific embodiment, the oscillation frequency is 60124±10 MHz and linearly modulated within a 50 MHz band around this frequency. The electromagnetic waves may be delivered with any electronic or photonic device known within the art. The electromagnetic waves may have a power density below 1 mW/cm$^2$, such as between 0.004 mW/cm$^2$ and 0.2 mW/cm$^2$, such as about 0.1 mW/cm$^2$.

According to one embodiment, said electromagnetic waves have a power density below 1 mW/cm$^2$; preferably said electromagnetic waves have a power density of between 0.004 mW/cm$^2$ and 0.2 mW/cm$^2$. Thus, the electromagnetic waves may have a power density of about 0.1 mW/cm$^2$.

According to another embodiment, said electromagnetic waves are modulated in a frequency within the range of 0.01% to about 0.5% of the average frequency.

According to a further embodiment, said yeast cell has been treated with electromagnetic waves for a time period of from 10 minutes to 240 minutes, such as from 20 minutes to 130 minutes, such as from 20 minutes to 120 minutes, such as from 30 minutes to 90 minutes, such as from 35 minutes to 85 minutes, such as 40 minutes, such as 50 minutes, such as 60 minutes, such as 70 minutes, such as 80 minutes.

According to yet another embodiment, said yeast cell is of the genus *Saccharomyces*, such as a yeast cell being selected from the group consisting of *Saccharomyces carlsbergensis* or *Saccharomyces cerevisiae*. An advantage with this is that such yeast may be readily available at a low cost.

The yeast cell may be *Saccharomyces cerevisiae*.

The yeast cell may be *Saccharomyces cerevisiae* S Ivovskaja-Milmed. This strain has been deposited as DSM 33148. The strain has previously been deposited as Y2483.

According to a second aspect of the present disclosure, a composition comprising at least one yeast cell according to the present disclosure and an excipient and/or a carrier is provided. The composition may be for use in the treatment and/or alleviation of allergy and/or symptoms caused by allergy. The composition may contain sterile wort, preferably 5 to 20 wt %, such as 8 to 15 wt %, such as 10 to 12 wt %, such as 11 wt %. The composition may contain a carbohydrate, such as glucose and/or saccharose. The composition may contain a vitamin and/or a mineral.

According to one embodiment, the composition is for oral intake. This is advantageous since it allows the patient to administer the composition him- or herself. Furthermore, oral intake gives a systemic effect via uptake in the gastrointestinal tract. The composition for oral intake may be a suspension.

The treated yeast may be distributed to the subject in any form suitable, such as a liquid, a powder, a gel or as pill.

A single dose may comprise $5\times10^6$ CFU/dose to $50{,}000\times10^6$ CFU/dose, such as $10\times10^6$ CFU/dose to $20{,}000\times10^6$ CFU/dose, such as $100\times10^6$ CFU/dose to $17{,}000\times10^6$ CFU/dose, such as $200\times10^6$ CFU/dose to $15{,}000\times10^6$ CFU/dose, such as $300\times10^6$ CFU/dose to $12{,}000\times10^6$ CFU/dose, such as $400\times10^6$ CFU/dose to $11{,}000\times10^6$ CFU/dose, such as $500\times10^6$ CFU/dose to $10{,}000\times10^6$ CFU/dose, such as $600\times10^6$ CFU/dose to $8{,}000\times10^6$ CFU/dose, such as $1{,}000\times10^6$ CFU/dose to $6{,}000\times10^6$ CFU/dose, such as $1{,}200\times10^6$ CFU/dose to $5{,}500\times10^6$ CFU/dose such as $2{,}000\times10^6$ CFU/dose to $5{,}000\times10^6$ CFU/dose, such as $2{,}500\times10^6$ CFU/dose to $4{,}500\times10^6$ CFU/dose such as $3{,}000\times10^6$ CFU/dose to $4{,}000\times10^6$ CFU/dose. CFU=colony forming unit.

Preferably, a single dose for humans comprises from $50\times10^6$ CFU/dose to $20{,}000\times10^6$ CFU/dose, such as $100\times10^6$ CFU/dose to $6{,}000\times10^6$ CFU/dose, such as $300\times10^6$ CFU/dose to $3{,}000\times10^6$ CFU/dose, such as $400\times10^6$ CFU/dose to $2{,}000\times10^6$ CFU/dose, such as $500\times10^6$ CFU/dose to $1{,}200\times10^6$ CFU/dose such as $600\times10^6$ CFU/dose to $1{,}000\times10^6$ CFU/dose.

Preferably, a single dose for a larger mammal, such as a horse or cow, comprises from $6{,}000\times10^6$ CFU/dose to $20{,}000\times10^6$ CFU/dose, such as $8{,}000\times10^6$ CFU/dose to $18{,}000\times10^6$ CFU/dose, such as $10{,}000\times10^6$ CFU/dose to $15{,}000\times10^6$ CFU/dose, such as $12{,}000\times10^6$ CFU/dose.

Preferably, a single dose for a smaller mammal, such as a rabbit, cat or dog, comprises $10\times10^6$ CFUs/dose to $1{,}500\times10^6$ CFUs/dose, such as $100\times10^6$ CFU/dose to $1{,}000\times10^6$ CFU/dose, such as $200\times10^6$ CFU/dose to $800\times10^6$ CFU/dose, such as $300\times10^6$ CFU/dose to $600\times10^6$ CFU/dose, such as $500\times10^6$ CFU/dose.

Yeast cells according to the present disclosure may be administered in an amount of from $10\times10^6$ CFUs/day to $50{,}000\times10^6$ CFUs/day, such as $25\times10^6$ CFUs/day to $20{,}000\times10^6$ CFUs/day, such as $50\times10^6$ CFUs/day to $10{,}000\times10^6$ CFUs/day, such as $100\times10^6$ CFUs/day, such as $100\times10^6$ CFUs/day to $8{,}000\times10^6$ CFUs/day, such as $200\times10^6$ CFUs/day to $7{,}500\times10^6$ CFUs/day, such as $400\times10^6$ CFUs/day to $6{,}000\times10^6$ CFUs/day, such as $500\times10^6$ CFUs/day to $5{,}000\times10^6$ CFUs/day, such as $600\times10^6$ CFUs/day to $4{,}500\times10^6$ CFUs/day such as $700\times10^6$ CFUs/day to $4{,}000\times10^6$ CFUs/day, such as $800\times10^6$ CFUs/day to $3{,}000\times10^6$ CFUs/day, such as $900\times10^6$ CFUs/day to $2{,}500\times10^6$ CFUs/day, such as $1{,}200\times10^6$ CFUs/day to $2{,}000\times10^6$ CFUs/day such as $1{,}000\times10^6$ CFUs/day to $1{,}500\times10^6$ CFUs/day.

Yeast cells according to the present disclosure may be administered to a human in an amount of from $400\times10^6$ CFUs/day to $20{,}000\times10^6$ CFUs/day, such as $500\times10^6$ CFUs/day to $10{,}000\times10^6$ CFUs/day, such as $600\times10^6$ CFUs/day to $2{,}000\times10^6$ CFUs/day, such as $750\times10^6$ CFUs/day to $1{,}500\times10^6$ CFUs/day, such as $800\times10^6$ CFU/day to $1{,}200\times10^6$ CFU/day, such as $900\times10^6$ CFUs/day to $1{,}000\times10^6$ CFUs/day.

Yeast cells according to the present disclosure may be administered to a larger mammal, such as a horse or cow, in an amount of from $1{,}000\times10^6$ CFUs/day to $10{,}000\times10^6$ CFUs/day, such as $2{,}000\times10^6$ CFUs/day to $8{,}000\times10^6$ CFUs/day, such as $3{,}000\times10^6$ CFUs/day to $6{,}000\times10^6$ CFUs/day, such as $4{,}000\times10^6$ CFUs/day to $5{,}000\times10^6$ CFUs/day.

Yeast cells according to the present disclosure may be administered a smaller mammal, such as a rabbit, cat or dog, in an amount of from $10\times10^6$ CFUs/day to $2{,}000\times10^6$ CFUs/day, such as $50\times10^6$ CFUs/day to $1{,}500\times10^6$ CFUs/day, such as $100\times10^6$ CFUs/day to $1{,}000\times10^6$ CFUs/day, such as $200\times10^6$ CFUs/day to $800\times10^6$ CFUs/day, such as $300\times10^6$ CFUs/day to $600\times10^6$ CFUs/day, such as $400\times10^6$ CFUs/day to $500\times10^6$ CFUs/day.

Yeast cells according to the present disclosure may be administered in an amount of from $200\times10^6$ CFUs/week to $70{,}000\times10^6$ CFUs/week, such as $300\times10^6$ CFUs/week to $50{,}000\times10^6$ CFUs/week, such as $400\times10^6$ CFUs/week to $40{,}000\times10^6$ CFUs/week, such as $500\times10^6$ CFUs/week to $25{,}000\times10^6$ CFUs/week, such as $800\times10^6$ CFUs/week to $22{,}500\times10^6$ CFUs/week, such as $1{,}000\times10^6$ CFUs/week to $20{,}000\times10^6$ CFUs/week, such as $1{,}750\times10^6$ CFUs/week to $16{,}000\times10^6$ CFUs/week, such as $1{,}500\times10^6$ CFUs/week to $15{,}000\times10^6$ CFUs/week, such as $2{,}000\times10^6$ CFUs/week to $12{,}500\times10^6$ CFUs/week, such as $3{,}000\times10^6$ CFUs/week to $10{,}000\times10^6$ CFUs/week, such as $4{,}000\times10^6$ CFUs/week to $8{,}000\times10^6$ CFUs/week, such as $5{,}000\times10^6$ CFUs/week to $7{,}500\times10^6$ CFUs/week, such as $6{,}000\times10^6$ CFUs/week.

Yeast cells according to the present disclosure may be administered to a human in an amount of from $500\times10^6$ CFUs/week to $16{,}000\times10^6$ CFUs/week, such as from $800\times10^6$ CFUs/week to $12{,}500\times10^6$ CFUs/week, such as from $1{,}000\times10^6$ CFUs/week to $11{,}000\times10^6$ CFUs/week, such as from $2{,}000\times10^6$ CFUs/week to $10{,}000\times10^6$ CFUs/week, such as from $3{,}500\times10^6$ CFUs/week to $9{,}000\times10^6$ CFUs/week, such as from $4{,}000\times10^6$ CFUs/week to $8{,}500\times10^6$ CFUs/week such as from $4{,}500\times10^6$ CFUs/week to $8{,}000\times10^6$ CFUs/week, such as $5{,}000\times10^6$ CFUs/week to $7{,}000\times10^6$ CFUs/week, such as $6{,}000\times10^6$ CFUs/week.

Yeast cells according to the present disclosure may be administered to a larger mammal, such as a horse or cow, in an amount of from $7{,}000\times10^6$ CFUs/week to $70{,}000\times10^6$ CFUs/week, such as $10{,}000\times10^6$ CFUs/week to $50{,}000\times10^6$ CFUs/week, such as $15{,}000\times10^6$ CFUs/week to $40{,}000\times10^6$ CFUs/week, such as $16{,}000\times10^6$ CFUs/week to $35{,}000\times10^6$ CFUs/week, such as $20{,}000\times10^6$ CFUs/week to $30{,}000\times10^6$ CFUs/week, such as $22{,}000\times10^6$ CFUs/week to $27{,}000\times10^6$ CFUs/week, such as $24{,}000\times10^6$ CFUs/week to $26{,}000\times10^6$ CFUs/week, such as $25{,}000\times10^6$ CFUs/week.

Yeast cells according to the present disclosure may be administered a smaller mammal, such as a rabbit, cat or dog, in an amount of from $70\times10^6$ CFUs/week to $14{,}000\times10^6$ CFUs/week, such as $100\times10^6$ CFUs/week to $10{,}000\times10^6$ CFUs/week, such as $300\times10^6$ CFUs/week to $6{,}000\times10^6$ CFUs/week, such as $500\times10^6$ CFUs/week to $4{,}000\times10^6$ CFUs/week, such as $700 \times 10^6$ CFUs/week to $3,000 \times 10^6$ CFUs/week, such as $1,000 \times 10^6$ CFUs/week to $2,000 \times 10^6$ CFUs/week.

The time period for treatment may be at least two weeks, at least three weeks, at least four weeks, at least five weeks, at least six weeks, at least seven weeks, at least eight weeks, at least nine week or at least ten weeks. In certain cases, the treatment may be longer than ten weeks, e.g. when the allergy is pollen allergy or even continuous, e.g. when the allergy is fur allergy, mite allergy or food allergy.

According to one embodiment, the composition is a liquid composition.

In one specific embodiment, the composition is in the form of a malt beverage or in any kind of beverage comprising the treated yeast or yeast cells grow from treated yeast.

According to one embodiment, the liquid composition comprises the yeast cell in an amount of from $10 \times 10^6$ CFUs/mL to $50 \times 10^6$ CFUs/mL, preferably from $20 \times 10^6$ CFUs/mL to $40 \times 10^6$ CFUs/mL, such as $30 \times 10^6$ CFUs/mL. Such a composition may be administered one, two, three, four, five, six or seven times a week, preferably two or three times a week. The composition may be administered in an amount of 30 to 1,000 mL per week, such as 40 to 900 mL per week, such as 50 to 800 mL per week, such as 60 to 700 mL per week, such as 100 to 500 mL per week, such as 200 to 400 mL per week. The composition may be administered to a human in an amount of 20 to 1,000 mL per week, such as 30 to 800 mL per week, such as 40 to 750 mL/week, such as 50 to 500 mL per week, such as 60 to 400 mL per week, such as 75 to 300 mL per week, such as 100 to 200 mL per week, divided into two or three portions. The composition may be administered to a larger mammal, such as a horse or cow, in an amount of 500 to 1000 mL per week, such as 600 to 900 mL/week, such as 700 to 800 mL per week, divided into two or three portions. In one preferred embodiment a total of 200 mL of a composition comprising $30 \times 10^6$ CFUs/mL is administered per week, divided into two or three portions. In another preferred embodiment, a total of 40 to 800 mL, such as 100 to 500 mL, most preferred 200 mL, of a composition comprising $20 \times 10^6$ CFUs/mL is administered, especially to a human, per week, divided into two or three portions. In another preferred embodiment a total of 700 to 1000 mL, such as 800 or 900 mL, of a composition comprising $20 \times 10^6$ CFUs/mL is administered to a larger animal, such as a horse or cow, per week, divided into two or three portions.

The liquid composition may be administered in separate portions, each portion comprising from $200 \times 10^6$ to $50,000 \times 10^6$ CFU/portion, such as $400 \times 10^6$ to $20,000 \times 10^6$ CFU/portion, such as $500 \times 10^6$ to $10,000 \times 10^6$ CFU/portion, such as $600 \times 10^6$ to $5,000 \times 10^6$ CFU/portion, such as $750 \times 10^6$ to $3,500 \times 10^6$ CFU/portion, such as $1,000 \times 10^6$ to $3,000 \times 10^6$ CFU/portion, such as $1,200 \times 10^6$ to $2,500 \times 10^6$ CFU/portion, such as $1,500 \times 10^6$ to $2,000 \times 10^6$ CFU/portion.

According to one embodiment, the composition is a powder composition.

In certain cases, the powder composition may comprise viable, dried yeast. The dried yeast may be prepared from a suspension of yeast cells in wort, such as 5 to 20 wt %, such as 8 to 15 wt %, such as 10 to 12 wt %, such as 11 wt %. Drying of yeast is a standard procedure well known to the skilled person.

In certain cases, the powder composition may comprise viable, freeze-dried treated yeast. The freeze-dried yeast may be prepared from a suspension of yeast cells in wort, such as 5 to 20 wt %, such as 8 to 15 wt %, such as 10 to 12 wt %, such as 11 wt %. Freeze-drying of yeast is a standard procedure well known to the skilled person.

The powder composition may comprise carbohydrates, such as glucose and/or saccharose.

The powder composition may comprise a vitamin and/or a mineral.

The powder composition may be administered one, two, three, four, five, six or seven times a week times a week. Alternatively, the powder composition may be administered one, two, three or four times a day, preferably two to three times a day.

The powder composition may be suspended in a liquid, such as water or aqueous beverage, such as a juice, before intake. The liquid may comprise carbohydrates, such as glucose and/or saccharose. When the powder composition comprises carbohydrates, such as glucose and/or saccharose, the powder composition may be suspended in water. The liquid may comprise a vitamin and/or a mineral. The powder composition is preferably suspended to a concentration of from $10 \times 10^6$ CFUs/mL to $50 \times 10^6$ CFUs/mL, preferably from $20 \times 10^6$ CFUs/mL to $40 \times 10^6$ CFUs/mL, such as $30 \times 10^6$ CFUs/mL.

The powder composition may be formulated as a capsule or tablet for oral intake. Preferably, such a capsule or tablet comprises from $300 \times 10^6$ CFU/capsule or tablet to $7,000 \times 10^6$ CFU/capsule or tablet, such as $400 \times 10^6$ CFU/capsule or tablet to $6,750 \times 10^6$ CFU/capsule or tablet, such as $500 \times 10^6$ CFU/capsule or tablet to $6,500 \times 10^6$ CFU/capsule or tablet, such as $750 \times 10^6$ CFU/capsule or tablet to $6,000 \times 10^6$ CFU/capsule or tablet, such as $1,000 \times 10^6$ CFU/capsule or tablet to $5,000 \times 10^6$ CFU/capsule or tablet, such as $1,200 \times 10^6$ CFU/capsule or tablet to $4,500 \times 10^6$ CFU/capsule or tablet, such as $2,000 \times 10^6$ CFU/capsule or tablet to $4,000 \times 10^6$ CFU/capsule or tablet, such as $2,500 \times 10^6$ CFU/capsule or tablet to $3,500 \times 10^6$ CFU/capsule or tablet, such as $3,000 \times 10^6$ CFU/capsule or tablet.

Such a capsule or tablet may be administered one, two, three, four, five, six or seven times a week, preferably two or three times a week.

Such a capsule or tablet for intake two or three times a week preferably comprises from $400 \times 10^6$ CFU/capsule or tablet to $6,000 \times 10^6$ CFU/capsule or tablet, such as $1,200 \times 10^6$ CFU/capsule or tablet to $5,500 \times 10^6$ CFU/capsule or tablet, such as $1,000 \times 10^6$ CFU/capsule or tablet to $5,000 \times 10^6$ CFU/capsule or tablet, such as $2,000 \times 10^6$ CFU/capsule or tablet to $4,000 \times 10^6$ CFU/capsule or tablet, such as $3,000 \times 10^6$ CFU/capsule or tablet.

Alternatively, one capsule or tablet may be administrated orally once a day. Such a capsule or tablet for daily intake preferably comprises from comprising $100 \times 10^6$ CFUs to $3,000 \times 10^6$ CFUs, such as $200 \times 10^6$ CFUs to $2,500 \times 10^6$ CFUs, such as $300 \times 10^6$ CFUs to $2,000 \times 10^6$ CFUs, $500 \times 10^6$ CFUs to $1,500 \times 10^6$ CFUs, such as $750 \times 10^6$ CFUs to $1,500 \times 10^6$ CFUs, such as $800 \times 10^6$ CFU/capsule to $1,200 \times 10^6$ CFU/capsule, such as $900 \times 10^6$ CFUs, is administered per day.

The composition according to the present disclosure is obtainable by a method comprising the steps: preparing a growth medium; sterilizing or pasteurizing the growth medium; growing yeast cells in the growth medium; and treating the yeast with electromagnetic waves, wherein the electromagnetic waves is in the range of 30 GHz to 300 GHz. The electromagnetic waves is preferably within the range from about 1 to 300 GHz, such as 1 to 200 GHz, more preferably 10 to 100 GHz, such as 30 to 70 GHz, such as 35 to about 65 GHz, such as 40 to 65 GHz, such as 40 GHz, 41 GHz, 42 GHz, 43 GHz, 44 GHz, 45 GHz, 46 GHz, 47 GHz, 48 GHz, 49 GHz, 50 GHz, 51 GHz, 52 GHz, 53 GHz, 54 GHz, 55 GHz, 56 GHz, 7 GHz, 58 GHz, 59 GHz, 60 GHz, 61 GHz, 62 GHz, 63 GHz, 64 GHz or 65 GHz. Preferably, the oscillation frequency is 42194±10 MHz and linearly modulated within 100 MHz band around this frequency.

In one preferred embodiment, the oscillation frequency is 42194±10 MHz and linearly modulated within a 100 MHz band around this frequency.

In another preferred embodiment, the oscillation frequency is 53534±10 MHz and linearly modulated within a 50 MHz band around this frequency.

In another preferred embodiment the oscillation frequency is 60124±10 MHz and linearly modulated within a 50 MHz band around this frequency. The electromagnetic waves may be delivered with any electronic or photonic device known within the art, such as a YAV-1 therapeutic device, based on an IMPATT diode oscillator. The electromagnetic waves may have a power density below 1 $mW/cm^2$, such as between 0.004 $mW/cm^2$ and 0.2 $mW/cm^2$, e.g. about 0.1 $mW/cm^2$.

The present disclosure also provides a method for treating and/or alleviating allergy and/or symptoms caused by allergy, wherein the method comprises administering, to a subject in need thereof, a yeast cell that has been treated with electromagnetic waves in the range of 1 GHz to 300 GHz, or a yeast cell that has been grown from a yeast cell treated with electromagnetic waves in the range of 1 GHz to 300 GHz as explained above.

The subject may be any mammal, such as e.g. a human. Further, the mammal may be a domestic mammal, such as a horse, a cow, a camel, a cat or a dog. EHF energy is thus transferred into the treated subject in form of treated yeast externally stimulated by EHF radiation.

The invention can be implemented in any suitable form including food products, feed, other drink products, etc., or any combination of these, without departing from the gist of the invention.

EHF-Treatment

The effect of the EHF (extremely high frequency) treatment is shown in FIG. 1 (also described in WO 2011/023769).

Figure 1B:
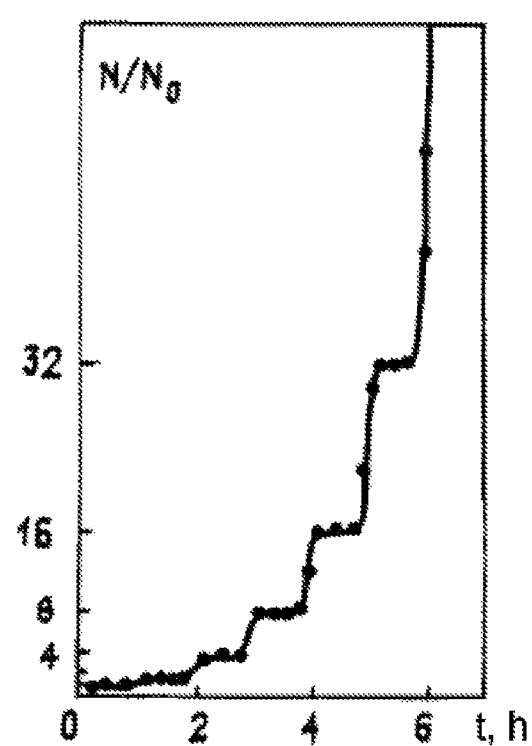
FIG. 1B is a diagram showing a growth curve of treated cells.

FIG. 1A is a growth curve of untreated cells. $N/N_0$ (Y axis) is the ratio of the number of cells N in the culture to the starting number $N_O$ and t (in hours, X axis) is the culture-development time. FIG. 1B is a growth curve of treated cells. The frequencies of the oscillations generated by the cells can be synchronized by corresponding reorganization of the information structures of the cells, which causes differences in the division-cycle durations of individual cells to be practically eliminated with the result of "steps" on the growth curve. It is apparent from FIG. 1B that after each division cycle the number of cells is doubled synchronously, so that the dependence of the number of cells on time is represented by a step curve.

Table 1 is an overview of the minimum time ($t_0$, min) needed to synchronize cell division of all cells at different power density levels (P, $mW/cm^2$) with a radiation frequency 42.2 GHz.

TABLE 1

The minimum time ($t_0$, min) needed to synchronize cell division of all cells at different power density levels (P, $mW/cm^2$) with a radiation frequency 42.2 GHz.

| $t_0$, min | P, $mW/cm^2$ |
|---|---|
| 126 | 0.005 |
| 103 | 0.009 |

TABLE 1-continued

The minimum time ($t_0$, min) needed to synchronize cell division of all cells at different power density levels (P, $mW/cm^2$) with a radiation frequency 42.2 GHz.

| $t_0$, min | P, $mW/cm^2$ |
|---|---|
| 81 | 0.015 |
| 60 | 0.026 |
| 49 | 0.040 |
| 38 | 0.077 |
| 36 | 0.130 |
| 34 | 0.209 |

Table 2 is an overview of time required ($t_0$, min) to synchronize cell division of 15 percent of the cells at different power density levels (P, $mW/cm^2$) with a radiation frequency of 42.2 GHz.

TABLE 2

Time required ($t_0$, min) to synchronize cell division of 15 percent of the cells at different power density levels (P, $mW/cm^2$) with a radiation frequency of 42.2 GHz

| $t_0$, min | P, $mW/cm^2$ |
|---|---|
| 111 | 0.003 |
| 86 | 0.006 |
| 65 | 0.012 |
| 45 | 0.024 |
| 38 | 0.037 |
| 33 | 0.052 |
| 31 | 0.074 |
| 27 | 0.130 |
| 26 | 0.200 |

Thus, a preferred EHF treatment time is between 20 and 120 minutes.

The method may further comprise the step of growing the treated yeast cells in the growth medium. The growth may be aborted at any time, when a desired cell concentration is achieved.

The growth medium may be wort, i.e. a tonic malt beverage obtained from wort and yeast. Any kind of yeast may be used. Any kind of wort may be used. Alternatively, the wort is obtained from a brewery or is made from barley malt or made from wort concentrates.

The wort may be pasteurized such as by heating it to between 70 and 75° C. for more than 30 minutes. The wort may then be stored in sealed containers up to 2 weeks at temperatures between 18 and 20° C.

*S. cerevisiae* may be revived by suspension in a small volume of sterilized 11 wt % wort. It is important that no other microorganisms contaminate the wort.

The revived culture is subsequently inoculated on a number of Petri dishes with agarized wort, to obtain pure yeast culture. This may be confirmed by microscope.

Prior to EHF-treatment, yeast from one of the dishes with sterile pure culture are transferred into a tube containing sterile 11 wt % wort, such as between 10 to 12 mL. The cultures are grown until skim appears, typically at 25 to 28° C. during 20 to 24 hours.

The yeast culture is then treated in an EHF-field. This may be done by first filling sterile Petri dishes with yeast suspension. The dish is then covered and placed in an EHF-unit. Such a unit may be any unit generating electromagnetic oscillations in the EHF-range. EHF-treating time is less than 240 minutes, such as less than 130 minutes, such as less than 120 minutes, such as less than 110 minutes, such as less than 100 minutes, preferably less than 90 minutes, such as 85 minutes, such as 80 minutes, such as 70 minutes, such as 60 minutes, such as 50 minutes, such as 40 minutes. The power density of EHF-oscillations is preferably about 0.1 mW/cm$^2$. The oscillation frequency is within the range of 30 to 300 GHz. The electromagnetic waves may be within the range from about 35 to about 65 GHz, such as 40 GHz, 41 GHz, 42 GHz, 43 GHz, 44 GHz, 45 GHz, 46 GHz, 47 GHz, 48 GHz, 49 GHz, 50 GHz, 51 GHz, 52 GHz, 53 GHz, 54 GHz, 55 GHz, 56 GHz, 57 GHz, 58 GHz, 59 GHz, 60 GHz, 61 GHz, 62, GHz, 63 GHz, 64 GHz, or 65 GHz.

In a specific embodiment, the oscillation frequency is 42194±10 MHz and linearly modulated within a 100 MHz band around this frequency.

In another specific embodiment, the oscillation frequency is 53534±10 MHz and linearly modulated within a 50 MHz band around this frequency.

In yet another specific embodiment, the oscillation frequency is 60124±10 MHz and linearly modulated within a 50 MHz band around this frequency.

The electromagnetic waves may be delivered with any electronic or photonic device known within the art, such as a YAV-1 therapeutic device, based on an IMPATT diode oscillator.

The frequency modulation of the electromagnetic waves may be from 0% to about 0.5% of the respective average frequency, such as 0.5% of the respective average frequency.

After treatment in the EHF-unit, the abovementioned treated suspension is transferred to a tube, such as a 50 to 100 mL tube, containing sterile 11 wt % wort. The cells are allowed to grow until skim appears, typically during 20 to 24 hours at 25 to 28° C. This is the seed material.

The seed material is then added to pasteurized or sterilized wort, typically 2 to 3 L, filled in containers (tube, can, etc.) of nominal capacity slightly larger than the amount word, typically 4 to 5 L, and cultivated until a cell concentration of 30 million cells/mL is achieved, typically after 20 to 24 hours at 25 to 28° C.

If large volumes of beverage are produced, the above-mentioned treatment may be implemented in several stages by adding the result of a previous cultivation cycle as seeding material to sterile wort with a ration of 1:10 seeding material:wort. The cells are allowed to grow until skim appears, typically during 20 to 24 hours at 25 to 28° C. The last stage of the beverage production stage is deemed to be finished when a cell concentration no less than 30 million cells/mL is achieved.

Upon completion of the production stage the beverage is ready for consumption and may be transferred to suitable transport vessels, e.g. bottles or cans. If storage is required, the beverage may be cooled to about 2 to 6° C., such as 2 to 4° C. and may then be stored, such as up to three weeks.

Treated Yeast Cells

The following is an enabling embodiment of a production procedure. However, many different alternate production procedures are possible, which will be recognized by a person skilled in the art.

Wort was obtained from a brewery and the weight fraction of dry matter in the diluted wort was adjusted to 11 wt % (11 wt % wort).

The wort was sterilized in an autoclave chamber with a pressure of 0.05 MPa during 20 minutes and stored between 18 and 20° C.

Yeast, *S. cerevisiae* (DSM 33148) was revived by suspension in a small volume of sterilized 11 wt % wort under sterile conditions.

The yeast was inoculated on a number of Petri dishes with agarized wort, to obtain pure yeast culture. This was confirmed by microscope.

Prior to EHF-treatment, yeast from one of the dishes with pure culture sterile was transferred into the tube containing 11 mL of sterile 11 wt % wort. The cultures were grown at 28° C. during 20 to 24 hours until skim appeared.

The yeast culture was then treated in an EHF-field. This was done by first filling sterile Petri dishes with yeast suspension. The dish was then covered and placed in an EHF-unit, generating electromagnetic oscillations in the EHF-range. EHF-treating time was 80 minutes. The power density of EHF-oscillations was kept near 0.1 mW/cm$^2$. The oscillation frequency was 53534±10 MHz and was linearly modulated within a 50 MHz band around this frequency. The electromagnetic radiation was generated by a YAV-1 therapeutic device, based on an IMPATT diode oscillator.

After treatment in the EHF-unit, the abovementioned treated suspension was transferred to a tube of 75 mL containing sterile 11 wt % wort. The cells were allowed to grow during 22 hours at 28° C. until skim appears. This was the seed material.

The seed material was then added to 3 L pasteurized or sterilized wort filled in tubes of nominal capacity of 5 L and cultivated until a cell concentration of $30\times10^6$ CFUs/mL was achieved. These treated yeast cells were used in the studies described below.

EXPERIMENTS

Two studies were performed, a first study (Study A) wherein 22 patients with allergic problems were treated with a composition according to the present disclosure, and a follow-up study (Study B), wherein 8 patients with allergic problems were treated with a composition according to the present disclosure and 8 patients with allergic problems were treated with a composition comprising untreated yeast cells.

Taken together, the two studies demonstrate that the allergy level of patients receiving *Saccharomyces cerevisiae* treated as described in the present disclosure was clearly improved by the treatment, compared to a control group receiving untreated yeast cells. Furthermore, the two studies demonstrate that the results are repeatable.

Study A

A liquid composition according to the present invention was evaluated in a study performed from 1 February to 31 May 2019. The composition contained *Saccharomyces cerevisiae* (DSM 33148) at an amount of $30\times10^6$ CFUs/mL suspended in sterilized wort as described above. The yeast cells (*Saccharomyces cerevisiae* (DSM 33148)) had been treated as described above. The study included 22 persons (7 females, 19-88 years old, and 15 male, 15-71 years old) suffering from different kinds of allergy. The patients were instructed to drink 100 mL of the composition before breakfast two times per week, i.e. a total of 200 mL per week. At the start of the study, each patient filled in a form describing his or her symptoms of allergy in detail. After 10 weeks, each patient was asked to evaluate their symptoms of allergy and rate whether they had experienced any improvement of the symptoms of allergy. One patient (Patient 8 below) answered that he was not able to evaluate the effect, since he typically experienced allergic symptoms during the summer months only, i.e. not during the test period. Thus, he had not experienced any symptoms of allergy during the test period. Nevertheless, as the other patients, this patient did not report any side-effects. The result of the frequency evaluation is shown in Table 3 below.

TABLE 3

Frequency analysis concerning patient improvement (totally 22 patients), defined by no improvement, minor improvement, moderate improvement, marked improvement and symptom-free

| Score 1 to 10 (1 = no improvement; 10 = no symptom free) | Number of patients | Patients (%) | |
|---|---|---|---|
| 1 | 1 | 5% | No improvement |
| 2-3 | 0 | 0% | Minor improvement |
| 4-6 | 5 | 23% | Moderate improvement |
| 7-9 | 8 | 36% | Marked improvement |
| 10 | 8 | 36% | Symptom-free |

As can be seen in Table 3, 23% of the 22 patients experienced a moderate improvement of their symptoms of allergy. Notably, 36% of the 22 patients participating in the evaluation experienced a marked improvement of their symptoms of allergy and as many as 36% were completely symptom-free.

In addition, 11 out of the 22 patients have reduced their intake of conventional allergy medications.

TABLE 4

Means and Standard deviations of patients before and after above treatment.

| | Before Treatment | After Treatment | Number of weeks without complete treatment |
|---|---|---|---|
| Mean | 0 | 7.67* | 1.52 |
| STD | 0 | 2.48 | 0.51 |

*$p < 0.0001$, paired t-tests

As shown in Table 4, comparisons of before and after treatment self-report indicated that there was a significant treatment effect.

TABLE 5

Pearson correlational analysis between treatment and number of treatment-missed weeks.

| | Treatment Result | Missed weeks of treat. |
|---|---|---|
| Treatment Result | | 0.526* |
| Missed weeks of treat. | 0.526* | |

*$p < 0.014$

The correlational analysis between treatment results for each patient in relation to the number of weeks each patient showed treatment compliance is shown in Table 5. Notably, in certain cases the yeast was not administered (i.e. non-compliance).

Individual patients are described below. Each patient's comments are cited below following translation.

Patient 1: Female, 42 years old. Non-smoker. History of allergy: pollen, grass, mites, dog and cat). Tiredness, frequent colds. Nasal obstruction, sneezing, reduced ability to smell, itchy, watery and swollen eyes; heavy breathing, shortness of breath, wheezing breath, thick mucus, chest tightness. Intake of dose as described above from start every morning before breakfast for 8 weeks. Perceived improvement of allergic problems rated as 8; reduced need to take allergy medicine; is less tired.

Patient 2. Male, 69 years old. Non-smoker: History of allergy: fur, cats and dogs, contact/urine. Non-genetic. No childhood indications, onset 27 years previously, subscription-free medication. Symptoms throughout the year; throat constriction, hoarseness. Intake of dose as described above from start before breakfast. Perceived improvement rated as 10; no parallel medication; no colds since treatment with EHF-treated yeast as described herein.

Patient 3. Male, 27 years old. Non-smoker but uses snuff. History of allergy: pollen/grass-seasonal, April to August. Symptoms: runny-blocked nose, itchiness/pruritus, tears, redness. No childhood indications, onset 2 years previously. No treatments used. Non-genetic. Intake of dose as described above from start before breakfast. Perceived improvement rated as 10; no parallel medication; mild cold.

Patient 4. Female, 88 years old. Non-smoker: No childhood indications, onset 57 years previously. History of allergy: fur, cats and dogs, contact. Throughout the year. Throat constriction, hoarseness, sneezing. Use of a variety of prescribed medications against fur allergy. Non-genetic. Intake of dose as described above from start before breakfast. Perceived improvement rated as 10; no colds since treatment with EHF-treated yeast as described herein.

Patient 5. Male, 42 years old. Non-smoker. No childhood indications. Onset 11 years previously. History of allergy: pollen/grass-seasonal—April to August. Seasonal—May, June, July. Symptoms: runny-blocked nose, itchiness/pruritus. Medication: loratidine, nasal spray. Non-genetic. Intake of dose as described above from start before breakfast. Perceived improvement rated as 10; no colds or illness, since treatment with EHF-treated yeast as described herein.

Patient 6. Male, 49 years old. Non-smoker but uses snuff: No childhood indications. Onset 10 years previously. History of allergy: pollen/grass, seasonal: May to August. Symptoms: runny-blocked nose, swelling. Medication: loratidine, nasal spray. Non-genetic. Intake of dose as described above from start before breakfast. Perceived improvement rated as 10; no colds or illness since treatment with EHF-treated yeast as described herein.

Patient 7. Male, 41 years old. Non-smoker. No childhood indications. Onset 24 years previously. History of allergy: vegetation, pollen; seasonal—April to June Symptoms: runny-blocked nose, swelling, sneezing, itchiness/pruritus. Medication: use of a variety medication against allergy. Non-genetic. Intake of dose as described above from start before breakfast for 11 weeks, missed 3 weeks. Perceived improvement rated as 5; reduced need to take allergy medicine; less asthma; and more alert since treatment with EHF-treated yeast as described herein.

Patient 8. Male, 42 years old. Non-smoker. No childhood indications. Onset 18 years previously. History of allergy: pollen; seasonal—April to July. Symptoms: runny-blocked and swelling nose, itchiness, redness and swollen eyes. Medication: use of a variety medication against allergy. Non-genetic. Intake of dose as described above from start before breakfast for 10 weeks, missed 2 weeks. Perceived improvement rated as 8; no parallel medications; less asthma; more alert since treatment with EHF-treated yeast as described herein.

Patient 9. Male, 71 years old. Non-smoker. No childhood indications. Onset 48 years previously. History of allergy: horse, pollen; seasonal—April to June. Symptoms: runny-blocked nose, swelling, itchiness in eyes. Medication: use of a variety medication against allergy. Non-genetic. Intake of dose as described above from start before breakfast for 10 weeks. Perceived improvement rated as 10; no parallel medications; more alert since treatment with EHF-treated yeast as described herein.

Patient 10. Female, 51 years old. Smoker. No childhood indications. Onset 30 years previously. History of allergy: pollen; seasonal—April to July. Symptoms: runny-blocked nose, sneezing, swelling, itchiness in eyes. Medication: use of a variety medication against allergy. Non-genetic. Intake of dose as described above from start before breakfast for 13 weeks, missed 4-5 weeks. Perceived improvement rated as 8; reduced need to take allergy medicine; increased strength and resilience, less pain in joints since treatment with EHF-treated yeast as described herein.

Patient 11. Female, 34 years old. Non-smoker. No childhood indications. History of allergy: pollen; seasonal—April to July. Symptoms: runny-blocked nose, swelling, itchiness in eyes. Medication: use of a variety medication against allergy. Non-genetic. Intake of dose as described above from start before breakfast for 10 weeks, missed 2 weeks. Perceived improvement rated as 7; reduced need to take allergy medicine; more alert; better mental health since treatment with EHF-treated yeast as described herein.

Patient 12. Female, 46 years old. Non-smoker. Childhood indications: eczema, asthma/bronchial problems, allergic rhinitis, food hypersensitivity. History of allergy: pollen, grass, dust, mites, dog, cat, horse, timothy, hazelnut, almond, apple, kiwi, peach. Throughout the year: Symptoms: blocked nose, swelling, sneezing, itchiness, redness and swollen eyes; throat constrictions, cough, hoarseness, heavy breathing, shortness of breath, wheezing breath, thick mucus, pain in the chest. Medication: budesonid, terbutalin, omeprazole, betamethasone. Genetic. Intake of dose as described above from start before breakfast for 8 weeks. Perceived improvement rated as 8; reduced need to take allergy medicine; more alert; better health, less illness since treatment with EHF-treated yeast as described herein.

Patient 13. Male, 62 years old. Non-smoker but uses snuff. Childhood indications: eczema, asthma, allergic rhinitis. History of allergy: dust, cat, pollen; seasonal—April to July. Symptoms: runny-blocked nose, sneezing, loss of smell, itchiness, redness and swollen eyes, hoarseness. Medication: antihypertensive. Non-genetic. Intake of dose as described above from start before breakfast for 8 weeks. Perceived improvement rated as 8; no parallel medications since treatment with EHF-treated yeast as described herein.

Patient 14. Male, 48 years old. Non-smoker. Childhood indications: allergic rhinitis, food hypersensitivity. History of allergy: pollen, grass, dust, fur, dog, cat, horse, birch, apple, scents; seasonal—March to October Symptoms: blocked and swelling nose, sneezing, itchiness and watery eyes; itchiness, irritation and swollen oral cavity/pharynx; throat constrictions, cough, hoarseness, heavy breathing. Medication: loratadine. Non genetic. Intake of dose as described above from start before breakfast for 8 weeks. Perceived improvement rated as 6; reduced need to take allergy medicine since treatment with EHF-treated yeast as described herein.

Patient 15. Female, 44 years old. Non-smoker. No childhood indications. History of allergy: pollen, grass, dust, mites, dog, cat, horse. Throughout the year. Symptoms: blocked and swelling nose, sneezing, reduced sense of smell; itchiness, watery and swollen eyes; throat constrictions, heavy breathing, shortness of breath, wheezing breath, thick mucus, pressure on the chest. Medication: allergy medicine. Non-genetic. Intake of dose as described above from start before breakfast for 8 weeks. Perceived improvement rated as 8; very reduced need to take allergy medicine; more alert; better health, less illness since treatment with EHF-treated yeast as described herein.

Patient 16. Male, 34 years old. Non-smoker but uses snuff. Childhood indications: allergic rhinitis. Onset 20 years previous. Medication: loratadine and mometasonfuroate. History of allergy: pollen, grass, dust, fur, dog, cat, horse; seasonal—April to September. Symptoms: blocked and swelling nose, sneezing; itchiness, watery and red eyes. Non-genetic. Intake of dose as described above from start before breakfast for 9 weeks, missed 1 week. Perceived improvement rated as 7; no parallel allergy medication since treatment with EHF-treated yeast as described herein, treatment with EHF-treated yeast as described herein has replaced the previous allergy medicine.

Patient 17. Male, 29 years old. Non-smoker but uses snuff. Childhood indications: allergic rhinitis. Medication; loratidine. History of allergy: pollen; seasonal—June to July, Symptoms: sneezing. Non-genetic. Intake of dose as described above from start before breakfast for 10 weeks missed 2 weeks. Perceived improvement rated as 4; no parallel allergy medication since treatment with EHF-treated yeast as described herein, treatment with EHF-treated yeast as described herein has replaced the previous allergy medicine.

Patient 18. Male, 34 years old. Non-smoker but uses snuff. Childhood indications: eczema, asthma, allergic rhinitis, food hypersensitivity. History of allergy: pollen, grass, dust, fur, cat, horse, hazelnut, peanuts, all nuts, apple, kiwi, peach, exotic fruits, throughout the year. Symptoms: runny-blocked and swelling nose, sneezing; itchiness, watery and red eyes. Genetic. Intake of dose as described above from start before breakfast for weeks, missed 2 weeks Perceived improvement rated as 5; no parallel allergy medication, treatment with EHF-treated yeast as described herein has replaced the previous allergy medicine.

Patient 19. Male, 45 years old. Non-smoker but uses snuff. No childhood indications. History of allergy: grass; seasonal—May to June. Symptoms: runny-blocked nose, itchiness in eyes. Medication: Non. Non-genetic. Intake of dose as described above from start before breakfast for 9 weeks missed 1 week. Perceived improvement rated as 6; treatment with EHF-treated yeast as described herein has replaced the previous allergy medicine with good effect.

Patient 20. Male, 42 years old. Non-smoker but uses snuff. No childhood indications. History of allergy: pollen; seasonal—May to July. Symptoms: sneezing, blocked nose, redness and itchiness in eyes. Medication: Non. Non-genetic. Intake of dose as described above from start before breakfast for 10 weeks, missed 2 weeks. Perceived improvement rated as 10; no parallel medication.

Patient 21. Male, 30 years old. Non-smoker. Childhood indications: allergic rhinitis. History of allergy: grass, pollen; seasonal—April to August. Symptoms: sneezing, runny nose, itchiness and swollen eyes. Medication: Non. Non-genetic. Intake of dose as described above from start before breakfast for 9 weeks, missed 1 week. Perceived improvement rated as 1; parallel allergy medication.

Patient 22. Female, 19 years old. Non-smoker. Childhood indications: Asperger. History of allergy: pollen; seasonal—May to July Symptoms: sneezing, blocked and runny nose, itchiness and red eyes. Medication: lithium, quetiapin. Genetic. Intake of dose as described above from start before breakfast for 8 weeks. missed 2 weeks. Perceived improvement rated as 10; no parallel allergy medication; more alert since treatment with EHF-treated yeast as described herein.

Study B

This study was a follow-up to Study A on the effects of treatment with yeast cells treated according to the present disclosure (referred to as Milmed treatment) upon ongoing allergy symptoms among sufferers. Previously, it was observed that allergy symptoms were alleviated among the patients studied (Study A above), but in that study each patient was used as his or her own control through which the level of allergy was compared before and after the treatment with a composition according to the present disclosure.

In Study B, a control group of patients treated for 8 weeks with a composition comprising untreated yeast cells was compared with a group of patients treated for 8 to weeks (median: 8 weeks) with yeast cells treated according to the present disclosure. The procedures and methods applied previously were repeated. The purpose of this study was to (i) test the putative interventional effects of a composition according to the present disclosure upon allergy symptoms by comparisons of treated and untreated groups, and (ii) to replicate the findings of Study A.

The efficacy of treatment with a composition according to the present disclosure over at least 8 weeks was tested for by the patients' responses to several questionnaire health items, including patients' subjective judgements concerned the following questions:

A. Have you experienced any improvement due to the treatment associated with the alleviation of your allergy symptoms? Scale 1 to 10 (1=no improvement; 10=symptom free)?

B. Have you experienced any improvement due to the treatment in your general health status? Scale 1 to 10 (1=no improvement; 10=large improvement)?

Un-treated yeast cells: A liquid composition comprising untreated yeast cells was evaluated in a study performed during the time period of April 21 to Jun. 15, 2020. The composition contained *Saccharomyces cerevisiae* (which had not been treated as described in the application) at an amount of 30×106 CFUs/mL suspended in sterilized wort as described in the patent application. "Normal dose" refers to 200 mL of the composition per week.

Treated yeast cells: A liquid composition as described in the patent application was evaluated in a study performed during the time period of March 17 to Jun. 24, 2020. The composition contained *Saccharomyces cerevisiae* (DSM 33148) at an amount of 30×106 CFUs/mL suspended in sterilized wort as described in the patent application. The yeast cells (*Saccharomyces cerevisiae* (DSM 33148)) had been treated as in the patent application. "Normal dose" refers to 200 mL of the composition per week.

Participants: Sixteen patients presenting allergic problems (Males=8; Females=8), aged from 30 to 71-years-of-age participated in the study. The patients were recruited through word-of-mouth contacts among associates and acquaintances as well as announcements that identified individuals who expressed an interest due to ongoing allergy difficulties, and all expressed the desire to receive some form of respite from their allergy problems, which were debilitating to a greater or lesser degree.

Group receiving untreated yeast cells—Control group: Eight patients presenting allergic problems (Males=3; Females=5), aged from 30 to 65 years-of-age, were treated with untreated yeast cells for 8 weeks. After 8 weeks, each patient rated the perceived improvement on allergy on a scale of 1 to 10 (1=no improvement; 10=symptom free) and the perceived improvement in general health on a scale of 1 to 10 (1=no improvement; 10=large improvement).

Group receiving treated yeast cells—"Milmed" group: Eight patients presenting allergic problems (Males=5; Females=3), aged from 30 to 71 years-of-age, were treated with "Milmed" for 8 to 10 weeks. The median treatment time was 8 weeks. After the test period, each patient rated the perceived improvement on allergy on a scale of 1 to 10 (1=no improvement; 10=symptom free) and the perceived improvement in general health on a scale of 1 to 10 (1=no improvement; 10=large improvement). All patients who were treated for 10 weeks reported that they had perceived the same level of improvement on allergy and in general health also after 8 weeks.

Results: The results are summarized in Table 6 (control group) and Table 7 ("Milmed" group) as well as in Table 8 below. In summary, the results clearly demonstrate that allergy symptoms can be alleviated by the intake of a composition comprising yeast cells according to the present disclosure.

TABLE 6

Control group (untreated yeast cells). Frequency analysis concerning patient improvement (totally 8 patients), defined by no improvement, minor improvement, moderate improvement, marked improvement and symptom-free.

| Score 1 to 10 (1 = no improvement; 10 = symptom free) | Number of patients | Patients (%) | |
|---|---|---|---|
| 1 | 5 | 62.5% | No improvement |
| 2-3 | 3 | 37.5% | Minor improvement |
| 4-6 | 0 | 0% | Moderate improvement |
| 7-9 | 0 | 0% | Marked improvement |
| 10 | 0 | 0% | Symptom-free |

As can be seen in Table 6, all of the 8 patients in the control group experienced no improvement or only a minor improvement of their symptoms of allergy.

As can be seen in Table 7 below, 12.5% of the 8 patients in the group receiving treated yeast in accordance with the current invention, experienced a moderate improvement of their symptoms of allergy. Notably, 50% of the 8 patients experienced a marked improvement of their symptoms of allergy and as many as 37.5% were completely symptom-free. These results are in line with the results of Study A.

Thus, it clearly shown that the electromagnetically irradiated yeast performs better than non-irradiated yeast.

TABLE 7

"Milmed" group (treated yeast cells). Frequency analysis concerning patient improvement (totally 8 patients), defined by no improvement, minor improvement, moderate improvement, marked improvement and symptom-free.

| Score 1 to 10 (1 = no improvement; 10 = symptom free) | Number of patients | Patients (%) | |
|---|---|---|---|
| 1 | 0 | 0% | No improvement |
| 2-3 | 0 | 0% | Minor improvement |
| 4-6 | 1 | 12.5% | Moderate improvement |
| 7-9 | 4 | 50% | Marked improvement |
| 10 | 3 | 37.5% | Symptom-free |

As can be seen in Table 8, the results clearly show that the treatment with a composition according to the present disclosure ("Milmed treatment") markedly alleviated allergy symptoms among the patients who received compositions comprising treated *Saccharomyces cerevisiae* as described in the present disclosure.

TABLE 8

Responses of Milmed-treated (N = 8) and Non-treated (N = 8) patients presenting allergy symptoms and health characteristics.

| Group | Self-assessed Allergy level improvement on a scale from 1 to 10 | Self-assessed General Health Improvement on a scale from 1 to 10 |
|---|---|---|
| Treated ("Milmed" group) | 8.38 ± 0.62** | 7.38 ± 0.82** |
| Non-treated (Control group) | 1.50 ± 0.26 | 2.25 ± 0.49 |

*$p < 0.02$;
**$p < 0.01$, pairwise t-tests, independent samples

Conclusions: (i) the allergy level of patients receiving *Saccharomyces cerevisiae* treated as described in the present disclosure ("Milmed") was clearly improved by the Milmed treatment (8.38 versus 1.50, see Table 8), and (ii) the general health experience of patients receiving (*Saccharomyces cerevisiae* treated as described in the present disclosure ("Milmed")) was markedly improved (7.38 versus 2.25, see Table 8).

Individual patients are described below. Each patient's comments are cited below following translation.

Untreated Milmed Group: Descriptions and Individual Participants' Responses

Patient 1: Female, 55-years-old, Ex-smoker. Childhood indications; asthma/bronchial problems, allergic rhinitis, food hypersensitivity. History of allergy: fur, cats, horse and dogs, contact. Throughout the year: rhinorrhea, sneezing; eye itchiness; throat itching. Use of a variety of prescribed medications against fur allergy. Non-genetic. Intake of normal dose from start before breakfast for 8 weeks. Perceived improvement on allergy: scale of 1 to 10 rated self as 1 out of 10; Perceived improvement in general health: scale of 1 to 10 rated self as 1 out of 10.

Patient 2: Female, 44-years-old, Non-smoker. Childhood indications; Eczema, asthma/bronchial problems, allergic rhinitis, food hypersensitivity. History of allergy: pollen, hazelnut, apple, kiwi, peach. Seasonal, Mars-September. Symptoms: blocked nose, sneezing, itchiness, redness, and swollen eyes; heavy breathing, shortness of breath, pressure in the chest. Medication: desloratadine. Genetic. Intake of normal dose start before breakfast for 8 weeks. Perceived improvement on allergy: scale of 1 to 10 rated self as 1 out of 10; Perceived improvement in general health: scale of 1 to 10 rated self as 1 out of 10.

Patient 3: Female, 65-years-old, Non-smoker. No childhood indications. History of allergy: pollen, hazelnut. Seasonal, April-May. Symptoms: allergic rhinitis, sneezing; itchiness and watery eyes; itchiness in throat. Medication: desloratadine. Not genetic. Intake of normal dose start before breakfast for 8 weeks. Perceived improvement on allergy: scale of 1 to 10 rated self as 1 out of 10; Perceived improvement in general health: scale of 1 to 10 rated self as 1 out of 10.

Patient 4: Male, 32-years-old. Non-smoker but snuff. Childhood indications; Eczema, allergic rhinitis. History of allergy: pollen, grass, fur, dog, cat, horse. Seasonal, June-July. Symptoms: allergic rhinitis, blocked nose, impaired sense of smell, sneezing; itchiness, watery and swollen eyes; cough. Medication: antihistamine. Genetic. Intake of normal dose start before breakfast for 8 weeks. Perceived improvement on allergy: scale of 1 to 10 rated self as 1 out of 10; Perceived improvement in general health: scale of 1 to 10 rated self as 2 out of 10.

Patient 5: Male, 30-years-old. Non-smoker but snuff. Childhood indications; allergic rhinitis, cardiac asthma (type of coughing or wheezing that occurs with left heart failure). History of allergy: pollen, grass, fur, dog, cat, horse. Seasonal, June-July. Symptoms: allergic rhinitis, blocked nose, impaired sense of smell, sneezing; itchiness, watery and swollen eyes; cough. Medication: antihistamine. Genetic. Intake of normal dose start before breakfast for 8 weeks. Perceived improvement on allergy: scale of 1 to 10 rated self as 1; Perceived improvement in general health: scale of 1 to rated self as 2.

Patient 6: Female, 44-years-old, Non-smoker. Childhood indications: asthma/bronchial problems, allergic rhinitis. History of allergy: pollen and grass. Seasonal, May-August. Symptoms: allergic rhinitis, sneezing; itchiness, redness, and swollen eyes. Medication: desloratadine, rhinocort. Non-genetic. Intake of normal dose start before breakfast for 8 weeks. Perceived improvement on allergy: scale of 1 to 10 rated self as 2 out of 10; Perceived improvement in general health: scale of 1 to 10 rated self as 2 out of 10.

Patient 7: Male, 31-years-old. Smoker and snuffer. Childhood indications: allergic rhinitis. History of allergy: pollen, dog fur. Seasonal, Mars-September. Symptoms: blocked nose, sneezing; itchiness in eyes; cough. Intake of normal dose start before breakfast for 8 weeks. Perceived improvement on allergy: scale of 1 to 10 rated self as 2; Perceived improvement in general health: scale of 1 to 10 rated self as 5, more alert.

Patient 8: Female, 49-years-old, Non-smoker but snuff user. Childhood indications: eczema. History of allergy: pollen. Seasonal, Mars-October. Symptoms: allergic rhinitis; itchiness in eyes; cough, shortness of breath. Medication: cyklokapron. Intake of normal dose start before breakfast for 8 weeks. Perceived improvement on allergy: scale of 1 to 10 rated self as 3 out of 10; Perceived improvement in general health: scale of 1 to 10 rated self as 3 out of 10, reduced bowel- and/or stomach illness/disorders.

Treated Milmed Group: Participants' Descriptions and Responses

Patient 1: Male, 47-years-old, Non-smoker. Childhood indications; allergic rhinitis. History of allergy: pollen, grass, horses. Seasonal, May-September. Symptoms: blocked nose, sneezing; itchiness in eyes; irritation and itchiness in throat. Medication: insulin, blood pressure medication. Non-genetic. Intake of normal dose start before breakfast for 8 weeks. Perceived improvement on allergy, scale of 1 to 10 rated self as 9; perceived improvement in general health, scale of 1 to 10 rated self as 9, more alert, fewer colds; infections; stomach and bowel disorder; improved sleep since Milmed treatment.

Patient 2: Male, 71-years-old, Non-smoker. No childhood indications. History of allergy: pollen, dog, cat, horse, odors and mold. Seasonal, May-July. Symptoms: allergic rhinitis, sneezing; redness, itchiness and watery eyes; loose mucus. Not genetic. Intake of normal dose start before breakfast for 10 weeks. Perceived improvement on allergy, scale of 1 to 10 rated self as 10; Perceived improvement in general health, scale of 1 to 10 rated self as 8, fewer infections, colds, and pain in body since Milmed treatment.

Patient 3: Male, 42-years-old, Non-smoker but snuff. No childhood indications. History of allergy: pollen. Seasonal, April-May. Symptoms: allergic rhinitis, sneezing, lower sense of smell; redness, and watery eyes. Medication; antihistamines. Intake of normal dose start before breakfast for 10 weeks, missed treatment one week. Perceived improvement on allergy, scale of 1 to 10 rated self as 8; Perceived improvement in general health, scale of 1 to 10 rated self as 3, fewer colds since Milmed treatment.

Patient 4: Female, 41-years-old, 'Party-smoker'. No childhood indications. History of allergy: pollen, cat, chemicals, scents. Seasonal, Mars-September. Symptoms: allergic rhinitis, sneezing, blocked nose. All year January-December; itchiness in eyes; shortness of breath, difficulty breathing. Medication: gabapentin, saroten, esomeprasol, and diklofenak. Genetic. Intake of normal dose start before breakfast for 8 weeks. Perceived improvement on allergy, scale of 1 to 10 rated self as 5 out of 10; perceived improvement in general health, scale of 1 to 10 rated self as 5 out of 10 since Milmed treatment.

Patient 5: Male, 63-years-old, Non-smoker but snuff user. Childhood indications; eczema. History of allergy: pollen, dust, cat, scents. Seasonal, April-July. Symptoms: allergic rhinitis, sneezing, blocked nose, lower and ceased sense of smell; redness, itchiness, swollen and watery eyes; hoarseness, wheezing in the chest, loose and thick mucus. Medication; enalapril STADA. Not genetic. Intake of normal dose start before breakfast for 8 weeks, missed one week. Perceived improvement on allergy, scale of 1 to 10 rated self as 8; perceived improvement in general health, scale of 1 to 10 rated self as 8, less infections, eczema, skin rash and itchiness since Milmed treatment.

Patient 6: Female, 52-years-old, Non-smoker exposed to passive smoking. Childhood indications: allergic rhinitis, food sensitivity. History of allergy: pollen, dust, cold air. Symptoms: allergic rhinitis, sneezing (April-August); itchiness, redness, and swollen eyes (May-August). Dust and cold air, January-December. Medication: sumatriptan, migraine medication. Genetic. Intake of normal dose start before breakfast for 8 weeks. Perceived improvement on allergy, scale of 1 to 10 rated self as 7, out of 10; perceived improvement in general health, scale of 1 to 10 rated self as 7 out of 10, more alert, less colds and pain in body, better sleep since Milmed treatment.

Patient 7: Female, 46-years-old, Non-smoker. Childhood indications; allergic rhinitis, food sensitivity. History of allergy: pollen, grass, dog, cat, horse, fur, mites, dust, cold air, physical effort. Symptoms: blocked nose, sneezing, impaired sense of smell (January-December); itchiness, watery, and swollen eyes (April-September); wheezing in the chest, tough mucus, heavy breathing, difficult to breathe, pressure over the chest (January-December). Non-genetic. Intake of normal dose start before breakfast for 8 weeks. Perceived improvement on allergy, scale of 1 to 10 rated self as 10, out of 10; perceived improvement in general health, scale of 1 to 10 rated self as 9 out of 10, more alert, fewer colds and improved sleep since Milmed treatment.

Patient 8: Male, 30-years-old, Non-smoker but snuff user. Childhood indications: asthma/bronchial problems, allergic rhinitis. History of allergy: pollen, dust, cold air. Seasonal, April-September. Symptoms: allergic rhinitis, sneezing, blocked nose, lower and ceased sense of smell; redness, itchiness and watery eyes; irritation in throat; coughing, hoarseness, pressure on the chest, heavy breathing, loose and thick mucus. Medication, antihistamines. Non-genetic. Intake of normal dose start before breakfast for 10 weeks. Perceived improvement on allergy, scale of 1 to 10 rated self as 10; perceived improvement in general health, scale of 1 to 10 rated self as 10, more alert, fewer colds since Milmed treatment.

The invention claimed is:

1. A method of treatment and/or alleviation of allergy and/or symptoms caused by allergy, comprising administering to a subject in need thereof, a yeast cell, wherein the yeast cell has been treated with electromagnetic waves in the range of 1 GHz to 300 GHz, or said yeast cell has been grown from a yeast cell treated with electromagnetic waves in the range of 1 GHz to 300 GHz, thereby treating and/or alleviating allergy and/or symptoms caused by allergy in the subject.

2. The method according to claim 1, wherein the allergy is selected from the group consisting of allergic rhinitis, mite allergy, fur allergy, seasonal allergy, food allergy.

3. The method according to claim 1, wherein the allergy is caused by an allergen selected from the group consisting of mite, pollen, animal hair, and animal dander.

4. The method according to claim 1, wherein said electromagnetic waves are in the range from about 1 GHz to about 200 GHz.

5. The method according to claim 4, wherein said electromagnetic waves are chosen from group consisting of: 40 GHZ, 41 GHZ, 42 GHZ, 43 GHZ, 44 GHz, 45 GHz, 46 GHZ, 47 GHz, 48 GHZ, 49 GHz, 50 GHZ, 51 GHZ, 52 GHZ, 53 GHZ, 54 GHZ, 55 GHZ, 56 GHZ, 57 GHz, 58 GHZ, 59 GHz, 60 GHz, 61 GHz, 62 GHz, 63 GHz, 64 GHz and 65 GHz.

6. The method according to claim 1, wherein said electromagnetic waves have a power density below 1 $mW/cm^2$.

7. The method according to claim 1, wherein said electromagnetic waves are modulated in a frequency within the range of 0.01% to about 0.5% of the average frequency.

8. The method according to claim 1, wherein said yeast cell has been treated with electromagnetic waves for a time period of from 10 minutes to 240 minutes.

9. The method according to claim 1, wherein said yeast cell is of the genus *Saccharomyces*.

10. The method according to claim 1, wherein said electromagnetic waves are in the range from 40 to 65 GHz.

11. The method according to claim 1, wherein said electromagnetic waves have a power density of between 0.004 mW/cm2 and 0.2 mW/cm2.

12. The method according to claim 1, wherein said yeast cell has been treated with electromagnetic waves for a time period of from 20 minutes to 120 minutes.

13. The method according to claim 1, wherein said yeast cell is selected from the group consisting of *Saccharomyces carlsbergensis* or *Saccharomyces cerevisiae*.

14. The method according to claim 1, wherein the yeast cell is present in a composition further comprising an excipient and/or a carrier.

15. The method according to claim 14, wherein the composition is for oral intake.

16. The method according to claim 14, wherein the composition is a liquid composition.

17. The method according to claim 16, wherein the composition comprises the yeast cell in an amount of from $10\times10^6$ CFUs/mL to $50\times10^6$ CFUs/mL.

18. The method according to claim 14, wherein the composition is a powder composition.

19. The method according to claim 16, wherein the composition comprises the yeast cell in an amount of from $20\times10^6$ CFUs/mL to $40\times10^6$ CFUs/mL.

* * * * *